(12) United States Patent
Peyman

(10) Patent No.: US 9,191,568 B2
(45) Date of Patent: Nov. 17, 2015

(54) AUTOMATED CAMERA SYSTEM WITH ONE OR MORE FLUIDIC LENSES

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 14/461,263

(22) Filed: Aug. 15, 2014

(65) Prior Publication Data

US 2015/0042865 A1 Feb. 12, 2015

Related U.S. Application Data

(63) Continuation-in-part of application No. 13/793,199, filed on Mar. 11, 2013, which is a continuation-in-part of application No. 13/165,231, filed on Jun. 21, 2011, now Pat. No. 8,409,278, which is a continuation-in-part of application No. 11/426,224, filed on Jun. 23, 2006, now Pat. No. 7,993,399, which is a continuation-in-part of application No. 11/259,781, filed on Oct. 27, 2005, now abandoned.

(51) Int. Cl.

| A61B 3/10 | (2006.01) |
|---|---|
| G02C 5/00 | (2006.01) |
| A61B 3/00 | (2006.01) |
| A61B 3/14 | (2006.01) |
| A61B 3/02 | (2006.01) |
| H04N 5/232 | (2006.01) |

(Continued)

(52) U.S. Cl.
CPC .......... *H04N 5/23212* (2013.01); *A61B 1/0019* (2013.01); *A61B 3/12* (2013.01); *A61B 3/1225* (2013.01); *A61F 2/16* (2013.01); *A61F 2/1635* (2013.01); *A61F 2/1648* (2013.01); *A61F 2/1651* (2015.04); *G02B 3/14* (2013.01); *G02B 7/28* (2013.01); *G03B 13/32* (2013.01)

(58) Field of Classification Search
CPC .......... A61B 3/103; A61B 3/14; A61B 3/113; A61B 3/125; A61B 3/024; A61B 3/1015; G02C 5/00; G02C 7/02
USPC ......... 351/200, 205–206, 210, 219, 222, 246, 351/41, 159, 160 R, 161, 176
See application file for complete search history.

(56) References Cited

U.S. PATENT DOCUMENTS

| 4,373,218 A | 2/1983 | Schachar |
|---|---|---|
| 4,573,998 A | 3/1986 | Mazzocco |

(Continued)

OTHER PUBLICATIONS

De-Ying Zhang, Nicole Justis, Yu-Hwa Lo, "Integrated Fluidic Adaptive Zoom Lens", Optics Letters, vol. 29, Issue No. 24, pp. 2855-2857, dated Dec. 15, 2004.

(Continued)

*Primary Examiner* — Dawayne A Pinkney
(74) *Attorney, Agent, or Firm* — The Law Office of Patrick F. O'Reilly III, LLC

(57) ABSTRACT

An automated camera system is disclosed herein. The automated camera system includes a camera configured to capture an image of an object; at least one fluidic lens disposed between the camera and the object, the at least one fluidic lens having a chamber that receives a fluid therein; a fluid control system operatively coupled to the at least one fluidic lens, the fluid control system configured to insert, or remove, an amount of the fluid into, or from, the chamber of the at least one fluidic lens; and a Shack-Hartmann sensor assembly operatively coupled to the fluid control system, the Shack-Hartmann sensor assembly by means of the fluid control system configured to automatically control the amount of the fluid in the chamber of the at least one fluidic lens, thereby automatically focusing the camera so that the image captured of the object is in focus.

14 Claims, 12 Drawing Sheets

(51) Int. Cl.
   *G03B 13/32*   (2006.01)
   *G02B 7/28*    (2006.01)
   *A61F 2/16*    (2006.01)
   *G02B 3/14*    (2006.01)
   *A61B 3/12*    (2006.01)
   *A61B 1/00*    (2006.01)

(56) References Cited

U.S. PATENT DOCUMENTS

| | | | |
|---|---|---|---|
| 4,685,921 A | 8/1987 | Peyman | |
| 4,731,078 A | 3/1988 | Stoy et al. | |
| 4,816,031 A | 3/1989 | Pfoff | |
| 6,142,630 A | 11/2000 | Koester | |
| 6,186,628 B1 | 2/2001 | Van de Velde | |
| 6,595,642 B2 | 7/2003 | Wirth | |
| 6,673,067 B1 | 1/2004 | Peyman | |
| 6,806,988 B2 * | 10/2004 | Onuki et al. | 359/253 |
| 6,947,782 B2 | 9/2005 | Schulman et al. | |
| 7,182,780 B2 | 2/2007 | Terwee et al. | |
| 7,413,306 B2 | 8/2008 | Campbell | |
| 2002/0016629 A1 | 2/2002 | Sandstedt et al. | |
| 2003/0147046 A1 | 8/2003 | Shadduck | |
| 2005/0140922 A1 | 6/2005 | Bekerman et al. | |
| 2006/0106426 A1 | 5/2006 | Campbell | |
| 2007/0046948 A1 | 3/2007 | Podoleanu et al. | |
| 2007/0156021 A1 * | 7/2007 | Morse et al. | 600/167 |
| 2007/0211207 A1 | 9/2007 | Lo et al. | |
| 2008/0030682 A1 * | 2/2008 | Teige et al. | 351/206 |
| 2008/0158508 A1 * | 7/2008 | Kawashima et al. | 351/206 |

OTHER PUBLICATIONS

First office action on the merits (Non-Final Rejection) in U.S. Appl. No. 13/793,199, mailed on Jan. 9, 2014.
Second office action on the merits (Final Rejection) in U.S. Appl. No. 13/793,199, mailed on Mar. 6, 2014.
Third office action on the merits (Non-Final Rejection) in U.S. Appl. No. 13/793,199, mailed on Jul. 18, 2014.

* cited by examiner

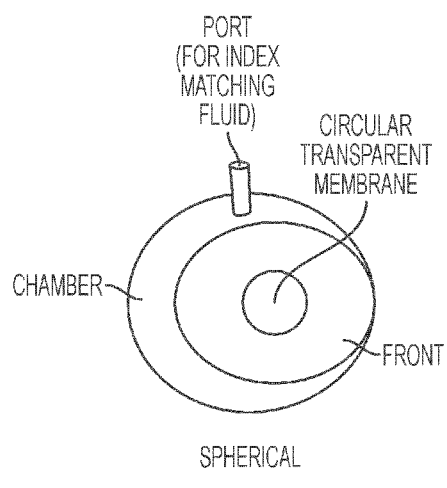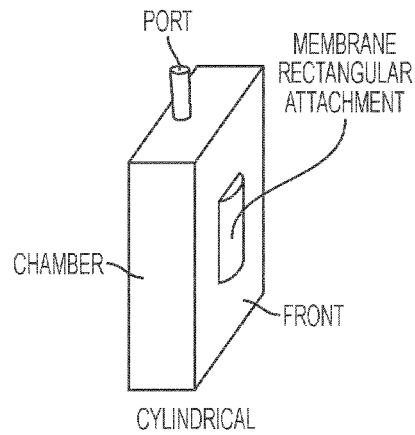
FIG. 12
FIG. 13

AUTOMATED CAMERA SYSTEM WITH ONE OR MORE FLUIDIC LENSES

CROSS-REFERENCE TO RELATED APPLICATIONS

This application is a continuation-in-part of application Ser. No. 13/793,199 entitled "Fluidic Adaptive Optic Fundus Camera", filed Mar. 11, 2013, which is a continuation-in-part of application Ser. No. 13/165,231 entitled "External Lens with Flexible Membranes for Automatic Correction of the Refractive Errors of a Person", filed Jun. 21, 2011, which is a continuation-in-part of application Ser. No. 11/426,224 entitled "External Lens Adapted to Change Refractive Properties", filed Jun. 23, 2006, which is a continuation-in-part of application Ser. No. 11/259,781, entitled "Intraocular Lens Adapted for Accommodation Via Electrical Signals", filed Oct. 27, 2005, the entire contents of each of which are hereby incorporated by reference.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to an automated camera system. More particularly, the invention relates to an automated camera system with one or more fluidic lenses.

2. Background

A normal emmetropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emmetropic eye, or a cornea or lens having a refractive power stronger than that of the cornea and lens of an emmetropic eye. This stronger refractive power causes the far point to be projected in front of the retina.

Conversely, a hypermetropic or hyperopic eye has an axial length shorter than that of a normal emmetropic eye, or a lens or cornea having a refractive power less than that of a lens and cornea of an emmetropic eye. This lesser refractive power causes the far point to be focused in back of the retina.

An eye suffering from astigmatism has a defect in the lens or shape of the cornea. Therefore, an astigmatic eye is incapable of sharply focusing images on the retina.

An eye can also suffer from presbyopia. Presbyopia is the inability of the eye to focus sharply on nearby objects, resulting from loss of elasticity of the crystalline lens.

Optical methods are known which involve the placement of lenses in front of the eye, for example, in the form of glasses or contact lenses, to correct vision disorders. A common method of correcting myopia is to place a "minus" or concave lens in front of the eye in order to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. Bifocal lenses can be used to correct presbyopia. The concave, convex or other shaped lenses are typically configured in the form of glasses or contact lenses.

Also, conventional cameras are known that require the users thereof to manually adjust the focus of a lens prior to taking a photograph so that the acquired image is in-focus. The manual adjustment of the camera lens is laborious and often inaccurate. Thus, what is needed is an automated camera system that comprises means for automatically focusing the camera without the necessity for manual adjustment by the user thereof, and without the need for moving parts on the camera itself.

BRIEF SUMMARY OF EMBODIMENTS OF THE INVENTION

Accordingly, the present invention is directed to lens systems for the human eye and an automated camera system with one or more fluidic lenses that substantially obviates one or more problems resulting from the limitations and deficiencies of the related art.

In accordance with one or more embodiments of the present invention, a lens system is provided. The lens system includes a lens adapted to be positioned along the main optical axis of the eye and a control unit. The control unit is operable with the lens to alter the focal length of the lens based at least partly upon a condition, such that the lens alters light rays and focuses the rays on the retina of the eye.

In accordance with one or more other embodiments of the present invention, a lens is provided. The lens includes a chamber adapted to house a substance. The lens is adapted to be positioned externally and relative to an eye and coupled to a control unit. The control unit is operable to control the focal length of the lens by influencing the substance, such control of the focal length altering light rays and focusing the light rays on the retina of the eye.

In accordance with yet one or more other embodiments of the present invention, a control unit is provided. The control unit includes an electronic circuit. The control unit is coupled to a lens, which includes a chamber adapted to house a substance. The lens is adapted to be positioned externally and relative to an eye. The electronic circuit is operable to control the focal length of the lens, such control of the focal length altering light rays and focusing the light rays on the retina of the eye.

In accordance with still one or more other embodiments of the present invention, an automated camera system is provided. The automated camera system includes a camera configured to capture an image of an object; at least one fluidic lens disposed between the camera and the object, the at least one fluidic lens having a chamber that receives a fluid therein; a fluid control system operatively coupled to the at least one fluidic lens, the fluid control system configured to insert an amount of the fluid into the chamber of the at least one fluidic lens, or remove an amount of the fluid from the chamber of the at least one fluidic lens, in order to change the shape of the at least one fluidic lens in accordance with the amount of fluid therein; and a Shack-Hartmann sensor assembly operatively coupled to the fluid control system, the Shack-Hartmann sensor assembly by means of the fluid control system configured to automatically control the amount of the fluid in the chamber of the at least one fluidic lens, thereby automatically focusing the camera so that the image captured of the object is in focus.

In a further embodiment of the present invention, the fluid control system comprises a pump and one or more fluid distribution lines, at least one of the one or more fluid distribution lines fluidly coupling the pump to the at least one fluidic lens so that the pump is capable of adjusting refractive power of the at least one fluidic lens.

In yet a further embodiment, the automated camera system further comprises a data processing device operatively coupled to the pump of the fluid control system and the Shack-Hartmann sensor assembly, wherein the data processing device is configured to control an operation of the pump of the fluid control system based upon one or more output signals from the Shack-Hartmann sensor assembly.

In still a further embodiment, the data processing device is further operatively coupled to the camera, wherein, when the Shack-Hartmann sensor assembly indicates to the data processing device that the object is in focus for the camera, the data processing device is configured to emit an initiation signal to the camera instructing the camera to capture the image of the object.

In yet a further embodiment, the Shack-Hartmann sensor assembly comprises a charge-coupled device (CCD) array and a lenslet array, and wherein the charge-coupled device (CCD) array of the Shack-Hartmann sensor assembly is operatively coupled to the data processing device.

In still a further embodiment, light is reflected back from the camera, and wherein the lenslet array is disposed in a path of the reflected light entering the Shack-Hartmann sensor assembly.

In yet a further embodiment, the automated camera system further comprises a dichroic mirror disposed in the path of the reflected light between the at least one fluidic lens and the lenslet array.

In still a further embodiment, the automated camera system further comprises a diffractive lens or a holographic optical element disposed in the path of the reflected light between the dichroic mirror and the lenslet array.

In accordance with yet one or more other embodiments of the present invention, an automated camera system is provided. The automated camera system includes a camera configured to capture an image of an object; a plurality of fluidic lenses disposed between the camera and the object, each of the plurality of fluidic lenses having a respective chamber that receives a fluid therein; a fluid control system operatively coupled to each of the plurality of fluidic lenses, the fluid control system configured to insert an amount of the fluid into the respective chamber of each of the plurality of fluidic lenses, or remove an amount of the fluid from the respective chamber of each of the plurality of fluidic lenses, in order to change the shape of each of the plurality of fluidic lenses in accordance with the amount of fluid therein; and a Shack-Hartmann sensor assembly operatively coupled to the fluid control system, the Shack-Hartmann sensor assembly by means of the fluid control system configured to automatically control the amount of the fluid in the respective chamber of each of the plurality of fluidic lenses, thereby automatically focusing the camera so that the image captured of the object is in focus.

In a further embodiment of the present invention, the fluid control system comprises a pump and a plurality of fluid distribution lines, at least two of the plurality of fluid distribution lines fluidly coupling the pump to respective ones of the plurality of fluidic lens so that the pump is capable of adjusting refractive power of the plurality of fluidic lens.

In yet a further embodiment, the automated camera system further comprises a data processing device operatively coupled to the pump of the fluid control system and the Shack-Hartmann sensor assembly, wherein the data processing device is configured to control an operation of the pump of the fluid control system based upon one or more output signals from the Shack-Hartmann sensor assembly.

In still a further embodiment, the data processing device is further operatively coupled to the camera, wherein, when the Shack-Hartmann sensor assembly indicates to the data processing device that the object is in focus for the camera, the data processing device is configured to emit an initiation signal to the camera instructing the camera to capture the image of the object.

In yet a further embodiment, the Shack-Hartmann sensor assembly comprises a charge-coupled device (CCD) array and a lenslet array, and wherein the charge-coupled device (CCD) array of the Shack-Hartmann sensor assembly is operatively coupled to the data processing device.

In still a further embodiment, the camera comprises one of: (i) a digital camera for photography, (ii) a camera for automated microscopy, (iii) an optical coherence tomography (OCT) camera, and (iv) a video surveillance camera.

In accordance with still one or more other embodiments of the present invention, an automated camera system is provided. The automated camera system includes a camera configured to capture an image of an object; three fluidic lenses disposed between the camera and the object, each of the three fluidic lenses having a respective chamber that receives a fluid therein; a fluid control system operatively coupled to each of the three fluidic lenses, the fluid control system configured to insert an amount of the fluid into the respective chamber of each of the three fluidic lenses, or remove an amount of the fluid from the respective chamber of each of the three fluidic lenses, in order to change the shape of each of the three fluidic lenses in accordance with the amount of fluid therein; and a Shack-Hartmann sensor assembly operatively coupled to the fluid control system, the Shack-Hartmann sensor assembly by means of the fluid control system configured to automatically control the amount of the fluid in the respective chamber of each of the three fluidic lenses, thereby automatically focusing the camera so that the image captured of the object is in focus.

In a further embodiment of the present invention, the three fluidic lenses include a spherical lens, a first cylindrical lens, and a second cylindrical lens.

In yet a further embodiment, the spherical lens is disposed in a first plane, the first cylindrical lens is disposed in a second plane, and the second cylindrical lens is disposed in a third plane, and wherein each of the first, second, and third planes are oriented generally parallel to one another.

In still a further embodiment, the first cylindrical lens has a first axis and the second cylindrical lens has a second axis, the first axis of the first cylindrical lens being disposed at an angle of approximately 45 degrees relative to the second axis of the second cylindrical lens.

In yet a further embodiment, the first plane of the spherical lens is disposed closer to the camera than the second plane of the first cylindrical lens and the third plane of the second cylindrical lens.

In still a further embodiment, the camera comprises one of: (i) a digital camera for photography, (ii) a camera for automated microscopy, (iii) an optical coherence tomography (OCT) camera, and (iv) a video surveillance camera.

Additional features and advantages are described herein, and will be apparent from, the following Detailed Description and the figures.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 12 illustrates a fluidic spherical lens in accordance with one embodiment of the present invention;

FIG. 13 illustrates a fluidic cylindrical lens in accordance with one embodiment of the present invention;

Throughout the figures, the same parts are always denoted using the same reference characters so that, as a general rule, they will only be described once.

DETAILED DESCRIPTION OF EMBODIMENTS OF THE INVENTION

In various embodiments, a lens capable of accommodation in response to electrical signals is provided. The lens can be placed at any suitable location along the optical path of an eye, including but not limited to within the capsular bag, in place of the capsular bag, within the posterior chamber or on, in or behind the cornea. Further, it should be noted that any suitable section of the capsular bag can be removed, including but not limited to an anterior portion or a posterior portion around the main optical axis of the eye. The lens is preferably coupled to a fluidic pumping system which is also coupled to a control system which preferably includes a power source and a signal generation unit.

Figure 1:
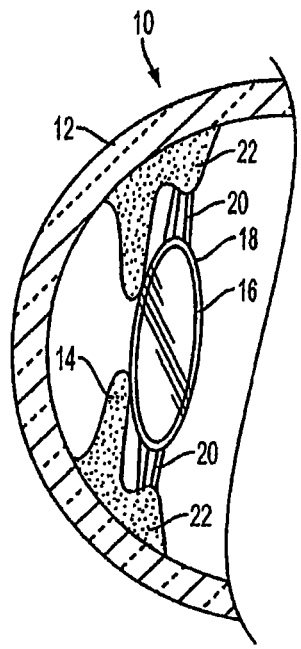
FIG. 1 is a side elevational view in section taken through the center of an eye showing the cornea, pupil, crystalline lens, and capsular bag.

Referring initially to FIG. 1, a normal eye 10 has a cornea 12, an iris 14, and a crystalline lens 16. The crystalline lens 16 is contained within a capsular bag 18 that is supported by zonules 20. The zonules 20, in turn, are connected to the ciliary muscle 22. According to Helmholz's theory of accommodation, upon contraction of the ciliary muscle 22, the tension on the zonules 20 is released. The elasticity of the lens causes the curvature of the lens 16 to increase, thereby providing increased refractive power for near vision. Conversely, during dis-accommodation, the ciliary muscle 22 is relaxed, increasing the tension on the zonules 20 and flattening the lens 16 to provide the proper refractive power for far vision.

Figure 2:
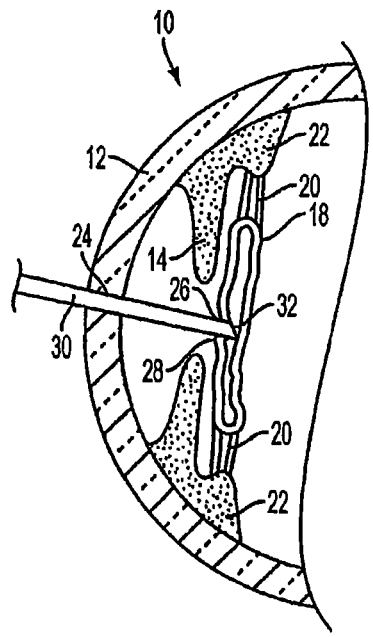
FIG. 2 is a side elevational view in section of the eye shown in FIG. 1 showing the capsular bag after removal of the crystalline lens.

If the electrically accommodating lens is to be positioned within the capsular bag and, thus, replace the crystalline lens, a suitable first step is to remove the existing lens. As illustrated in FIG. 2, the lens is preferably removed using any technique which allows removal of the lens through a relatively small incision, preferably about a 1-2 mm incision. The preferred method is to create a relatively small incision 24 in the cornea 12 and then perform a capsulorhexis to create an opening 26 into the anterior side 28 of the capsular bag 18. An ultrasonic probe 30 is inserted into the capsular bag 18 through the opening 26. The probe's vibrating tip 32 emulsifies the lens 16 into tiny fragments that are suctioned out of the capsular bag by an attachment on the probe tip (not shown). Alternatively, the lensectomy may be performed by laser phacoemulsification or irrigation and aspiration.

Once the crystalline lens 16 has been removed, the capsular bag 18 can be treated to help prevent a phenomenon known as capsular opacification. Capsular opacification is caused by the proliferated growth of the epithelial cells on the lens capsule. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells; however, it is often difficult to remove all of the unwanted cells. Furthermore, after time, the unwanted cells typically grow back, requiring further surgery. To prevent capsular opacification, the capsular bag 18 is preferably treated to eliminate the proliferated growth of epithelial cells, as described below.

Figure 3:
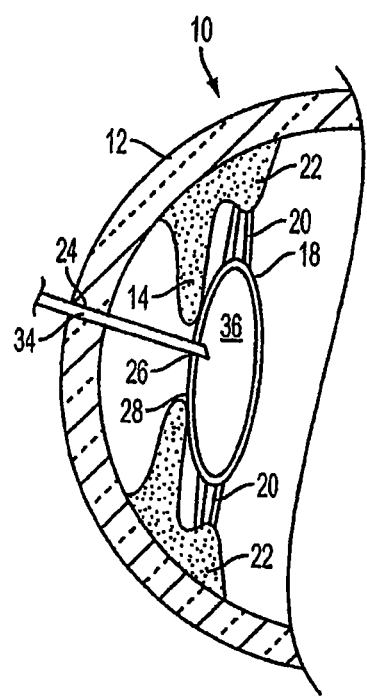
FIG. 3 is a side elevational view in section of the eye shown in FIG. 2 showing the treatment of the interior of the capsular bag with a liquid to prevent capsular opacification.

As seen in FIG. 3, one method of treating the epithelial cells to prevent capsular opacification is to use a cannula 34 to introduce a warm liquid 36 (preferably about greater 60° C.) into the capsular bag 18, filling the capsular bag 18. The liquid contains a suitable chemical that kills the remaining lens cells in the capsular bag and also cleans the interior of the capsular bag. Suitable chemicals, as well as other suitable methods of treatment that prevent capsular opacification are disclosed in U.S. Pat. No. 6,673,067 to Peyman, which is herein incorporated by reference in its entirety.

Figure 4:
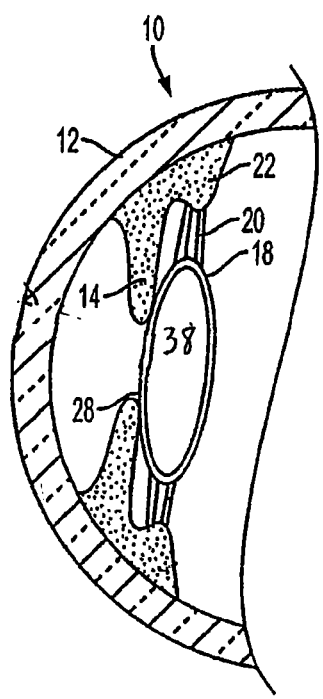
FIG. 4 is a side elevational view in section of the eye shown in FIG. 3 showing placement of a replacement lens into the capsular bag.
Figure 5:
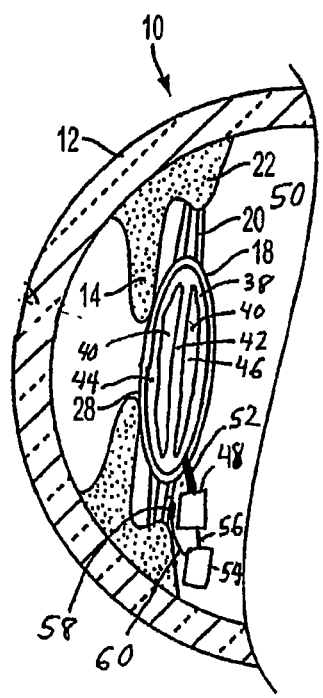
FIG. 5 is a side elevational view in section of the eye shown in FIG. 3 in which a replacement lens is positioned in the capsular bag and a fluidic system and remote power unit are positioned in the posterior chamber.

As shown in FIG. 4, a replacement lens 38 is then positioned within the capsular bag 18. Preferably, the lens 38 can be folded or rolled and inserted through the incision in the capsular bag 18; however, the lens 38 can be rigid and/or can be inserted through a larger second incision in the capsular bag 18 or the initial incision, possibly after the initial incision is widened, or in any other suitable manner. Preferably the lens 38 varies its focal length in response to changes in fluidic pressure within the lens made in accordance with electrical signals; however the lens 38 can change its index of refraction or alter its focal length in any other suitable manner. Since the capsular bag 18 is still in place, the capsular bag can still assist in accommodation; however, it is not necessary for capsular bag 18 to assist with accommodation. The lens, as shown in FIG. 5, preferably includes two chambers 40 set on opposite sides of a substrate 42 and covered with a flexible membrane 44; however, the lens can have one or any other suitable number of chambers. Preferably, the two chambers 40 contain a fluid 46, and preferably the fluid 46 is a sodium chromate solution; however, if desired, one or more of the chambers can contain something other than a fluid or the chambers can contain different fluids or different sodium chromate solutions. The substrate 42 is preferably glass; however, the substrate 42 can be any suitable material. Preferably, the flexible membrane 44 is a biocompatible material; however, the flexible membrane can be any suitable material.

Preferably, the fluidic pressure within the chambers 40 can be altered using a fluidic system 48 which includes a miniature fluidic pressure generator (e.g., a pump or any other suitable device), a fluid flow control device (e.g., a valve or any other suitable device), a control circuit and a pressure sensor; however, the fluidic pressure can be altered in any suitable manner. Further, if desired, a fluidic system 48 does not need a pressure sensor. When subjected to an electrical signal, the electronic control circuit of the fluidic system 48 controls the valves and pumps to adjust the fluidic pressure in one or more of the chambers 40. Preferably, the fluidic pressure is adjusted by pumping fluid in or releasing a valve to allow fluid to flow out and back into the system 48; however, the fluidic pressure can be adjusted by pumping fluid out or in any other suitable manner. As a result, the shape and the focal length of the lens 38 is altered, providing accommodation. Lenses that similarly change focal length in response to fluidic pressure changes made in accordance with electrical signals are described in greater detail in "Integrated Fluidic Adaptive Zoom Lens", *Optics Letters*, Vol. 29, Issue 24, 2855-2857, December 2004, the entire contents of which is hereby incorporated by reference.

As shown in FIG. 5, fluidic system 48 is preferably positioned in the posterior chamber 50; however, the fluidic system 48 can be positioned outside the eye, within the sclera, between the sclera and the choroids or any other suitable location. Further, the fluidic system 48 is preferably positioned such that it is not in the visual pathway. A tube 52 fluidly connects the lens 38 and the fluidic system 48. Preferably, the tube 52 passes through a small incision in the capsular bag 18 near the connection of the zonules 20 and the capsular bag 18; however, the tube 52 can pass through the capsular bag in any suitable location.

Preferably, fluidic system 48 includes a power source which is preferably rechargeable through induction or other suitable means such as generating and storing electrical energy using eye and/or head movement to provide the energy to drive the generator; however, fluidic system 48 can be connected to a remote power source 54 as shown in FIG. 5 or to any other suitable power source. Preferably, the remote power source 54 is located in the posterior chamber 50; however, the remote power source 54 can be positioned outside the eye (e.g., under the scalp, within a sinus cavity, under the cheek, in the torso or in any other suitable location), within the sclera, between the sclera and the choroids or any other suitable location. Further, the remote power source 54 is preferably positioned such that it is not in the visual pathway. The remote power source 54 is preferably electrically coupled to the fluidic system 48 by electrically conductive line 56; however, the remote power source 54 can be coupled to the fluidic system 48 in any suitable manner. Further, the remote power source 54 preferably includes a signal generator which can supply control signals to the fluidic system 48 via electrically conductive line 56; however, the remote power source 54 can be without a signal generator, if desired, or can supply control signals to the fluidic system 48 in any suitable manner. Similar remote power sources are described in more detail in U.S. Pat. No. 6,947,782 to Schulman et al. which is herein incorporated by reference in its entirety.

Preferably, the remote power source 54 is coupled to a sensor 58 by electrically conductive line 60; however, the remote power source 54 can be coupled to sensor 58 in any suitable manner. The sensor 58 is preferably a tension sensor positioned on the zonules 20 so that the sensor 58 detects the amount of tension present in the zonules 20; however, the sensor 58 can be a wireless signal sensor, a neurotransmitter sensor, a chemical sensor, a pressure sensor or any other suitable sensor type and/or can be positioned in or near the ciliary muscle 22, at or near the nerve controlling the ciliary muscle 22, in the capsular bag 18 or in any other suitable location. Preferably, the sensor 58 detects the eye's attempt to cause its lens to accommodate; however, the sensor 58 can detect a manual attempt to accommodate the lens 38 (e.g., input through a wireless controller) or any other suitable input. The information detected at the sensor 58 is relayed to the remote power source 54 via line 60, and the signal generator of the remote power source 54 generates a signal in accordance with the information. The signal is sent to the fluidic system 48, which adjusts the fluidic pressure in one or more of the chambers 40 accordingly. Thus, the eye's natural attempts to focus will result in accommodation of lens 38. Response of lens 38 may vary from that of the natural lens; however, the neural systems which control the ciliary muscle 22 (and therefore the tension on the zonules 20), are provided with feedback from the optic nerve and visual neural pathways. As a result, the neural system can learn and adjust to the characteristics of the lens 38.

Figure 6:
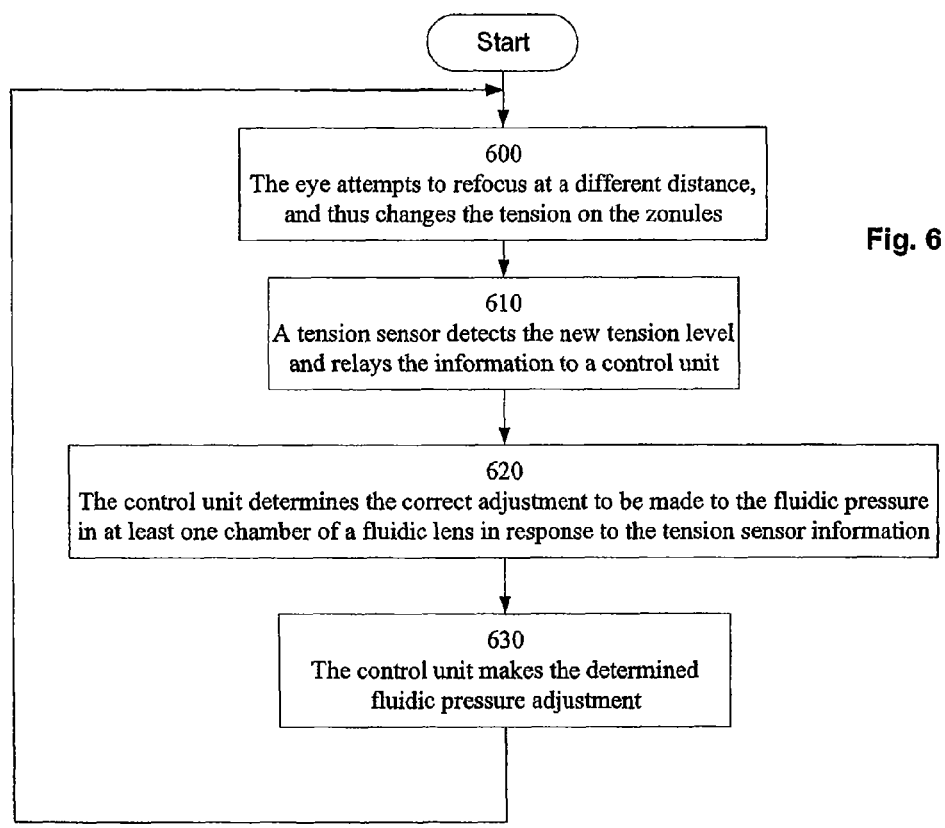
FIG. 6 is a flow chart of the process of accommodation in accordance with one embodiment of the present invention.

The process of accommodation in accordance with one embodiment is shown in FIG. 6. At step 600, the eye attempts to refocus at a different distance, and thus changes the tension on the zonules. At step 610, a tension sensor detects the new tension level and relays the information to a control unit. The control unit preferably includes a remote power source and a fluidic system; however, the control unit can include any suitable devices. At step 620, the control unit determines the correct adjustment to be made to the fluidic pressure in at least one chamber of a fluidic lens in response to the tension sensor information. At step 630, the control unit makes the determined fluidic pressure adjustment and the process repeats at step 600.

Figure 7:
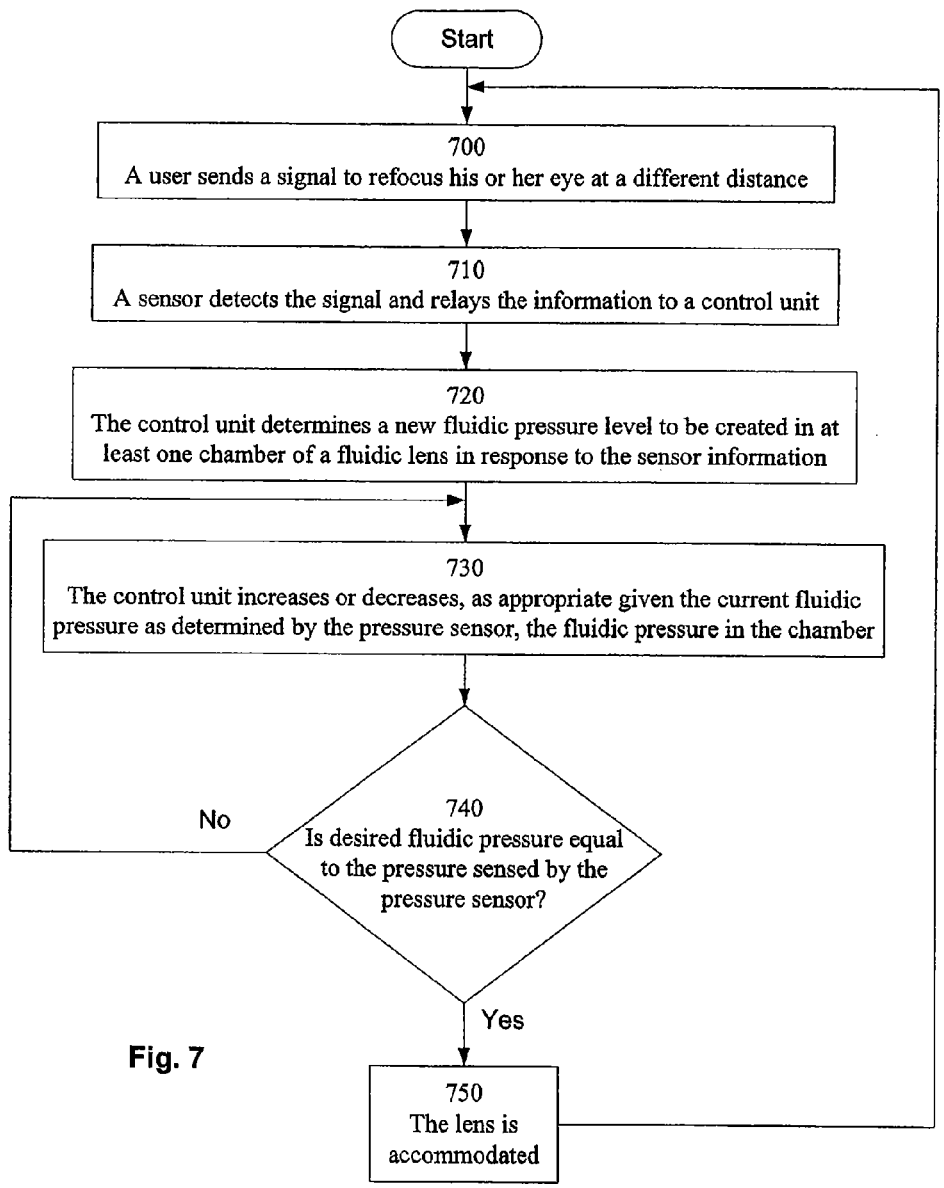
FIG. 7 is a flow chart of the process of accommodation in which the fluidic system includes a pressure sensor for sensing the pressure in at least one of the chambers in accordance with one embodiment of the present invention.

Another process of accommodation in accordance with another embodiment in which the fluidic system includes a pressure sensor for sensing the pressure in at least one of the chambers is shown in FIG. 7. At step 700, a user sends a signal to refocus his or her eye at a different distance. Preferably, the signal is sent wirelessly; however, the signal can be sent in any suitable manner. Further, the signal preferably includes information corresponding to the desired different distance; however, the signal can include information indicating only that the desired distance is closer or farther or any other suitable information. At step 710, a sensor detects the signal and relays the information to a control unit. The control unit preferably includes a remote power source and a fluidic system; however, the control unit can include any suitable devices. At step 720, the control unit determines a new fluidic pressure level to be created in at least one chamber of a fluidic lens in response to the sensor information. At step 730, the control unit increases or decreases, as appropriate given the current fluidic pressure as determined by the pressure sensor, the fluidic pressure in the chamber. At step 740, it is determined whether the desired fluidic pressure is equal to the pressure sensed by the pressure sensor. If the desired fluidic pressure is equal to the pressure sensed by the pressure sensor, at step 750, the lens is accommodated and the process repeats at step 700. If the desired fluidic pressure is not equal to the pressure sensed by the pressure sensor, the process repeats at step 730.

Figure 8:
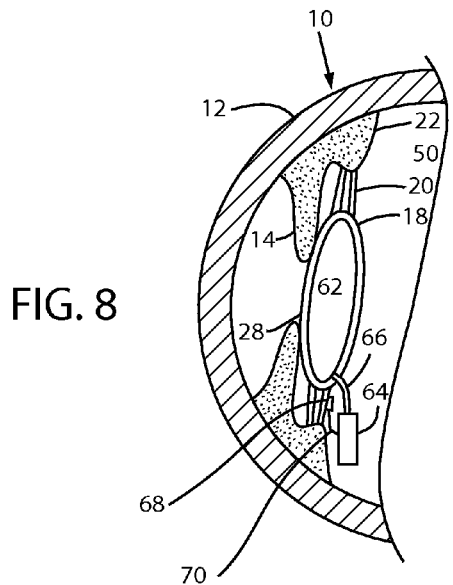
FIG. 8 is a side elevational view in section of the eye shown in FIG. 3 in which a replacement lens is positioned in the capsular bag and a power unit is positioned in the posterior chamber.

FIG. 8 illustrates an alternative accommodating lens 62. Lens 62 responds to electrical stimulation by changing its focal length. Similar to lens 38, lens 62 is preferably placed within the capsular bag 18; however, the lens 62 can be placed in the posterior chamber 50, in place of the capsular bag 18, within the cornea 12, on the surface of the eye or in any other suitable location. Further, it should be noted that any suitable section of the capsular bag can be removed, including but not limited to an anterior portion or a posterior portion around the main optical axis of the eye. If the lens 62 is placed within the capsular bag 18, the capsular bag can assist with accommodation; however, it is not necessary for the capsular bag 18 to assist with accommodation. Lens 62 may have one or more chambers that are at least partly filled with a fluid or other substance; however, lens 62 is not required to have a chamber.

Preferably, lens 62 is a fluid lens that alters its focal length by changing its shape; however lens 62 can be any suitable type of lens and can change its focal length in any suitable manner. The lens 62 preferably includes two immiscible (i.e., non-mixing) fluids of different refractive index (or other suitable optical property); however, the lens 62 is not required to include two immiscible fluids of different refractive index. Preferably, one of the immiscible fluids is an electrically conducting aqueous solution and the other an electrically non-conducting oil, contained in a short tube with transparent end caps; however, the immiscible fluids can be any suitable fluids and can be contained in any suitable container. The internal surfaces of the tube wall and one of its end caps are preferably coated with a hydrophobic coating that causes the aqueous solution to form itself into a hemispherical mass at the opposite end of the tube, where it acts as a spherically curved lens; however, the hydrophobic coating is not required and, if present, can be arranged in any suitable manner. Further, the coating can include any suitable material, including hydrophilic substances.

Preferably, the shape of the lens 62 can be adjusted by applying an electric field across the hydrophobic coating such that it becomes less hydrophobic (a process called "electrowetting" that results from an electrically induced change in surface-tension); however, the shape of the lens 62 can be adjusted by applying an electric field across any suitable portion of the lens 62. Preferably, as a result of this change in surface-tension, the aqueous solution begins to wet the sidewalls of the tube, altering the radius of curvature of the meniscus between the two fluids and hence the focal length of the lens. Increasing the applied electric field can preferably cause the surface of the initially convex lens to become less convex, substantially flat or concave; however increasing the applied electric field can cause the surface of the lens to change in any suitable manner. Preferably, decreasing the applied electric field has the opposite effect, enabling the lens 62 to transition smoothly from being convergent to divergent, or vice versa, and back again repeatably.

The lens 62 can measure 3 mm in diameter by 2.2 mm in length; however the lens 62 can have any suitable dimensions. The focal range of the lens 62 can be any suitable range and can extend to infinity. Further, switching over the full focal range can occur in less than 10 ms or any other suitable amount of time. Preferably, lens 62 is controlled by a DC voltage and presents a capacitive load; however, the lens 62 can be controlled by any suitable voltage and operate with any suitable electrical properties.

Lens 62 is electrically coupled to a power source 64 by electrically conductive line 66; however, lens 62 can be coupled to power source 64 in any suitable manner. Preferably, power source 64 is rechargeable through induction or other suitable means such as generating and storing electrical energy using eye and/or head movement to provide the energy to drive the generator; however, the power source 64 can be non-rechargeable, if desired. Similar to remote power source 54, the power source 64 is preferably located in the posterior chamber 50; however, the power source 64 can be positioned outside the eye (e.g., under the scalp, within a sinus cavity, under the cheek, in the torso or in any other suitable location), within the sclera, between the sclera and the choroids or any other suitable location. Further, the power source 64 is preferably positioned such that it is not in the visual pathway. The power source 64 preferably includes a signal generator which can supply current to the lens 62 via electrically conductive line 66; however, the power source 64 can be without a signal generator, if desired, or can supply control signals to the lens 62 in any suitable manner.

Preferably, the power source 64 is coupled to a sensor 68 by electrically conductive line 70; however, the power source 64 can be coupled to sensor 68 in any suitable manner. The sensor 68 is preferably a tension sensor positioned on the zonules 20 so that the sensor 68 detects the amount of tension present in the zonules 20; however, the sensor 68 can be a wireless signal sensor, a neurotransmitter sensor, a chemical sensor, a pressure sensor or any other suitable sensor type and/or can be positioned in or near the ciliary muscle 22, at or near the nerve controlling the ciliary muscle 22, in the capsular bag 18 or in any other suitable location. Preferably, the sensor 68 detects the eye's attempt to cause its lens to accommodate; however, the sensor 68 can detect a manual attempt to accommodate the lens 62 (e.g., input through a wireless controller) or any other suitable input. The information detected at the sensor 68 is relayed to the power source 64 via line 70, and the signal generator of the power source 64 generates a signal in accordance with the information. The signal is sent and passed through the lens 62, which preferably changes shape as a result of the electrical current flowing through it; however, the lens 62 could change its index of refraction in response to the electrical current flowing through it or change its focal length in any other suitable manner. Preferably, line 70 includes two separate electrical pathways that electrically couple to lens 62 at different, preferably substantially opposite, locations so that one of the pathways can serve as a ground wire; however, the lens 62 can be grounded in any other suitable manner to enable current supplied via line 70 to flow through the lens 62. As a result, similar to lens 38, the eye's natural attempts to focus will result in accommodation of lens 62. Response of lens 62 may vary from that of the natural lens; however, as with lens 38, the neural systems which control the ciliary muscle 22 (and therefore the tension on the zonules 20), are provided with feedback from the optic nerve and visual neural pathways. As a result, the neural system can learn and adjust to the characteristics of the lens 62.

Figure 9:
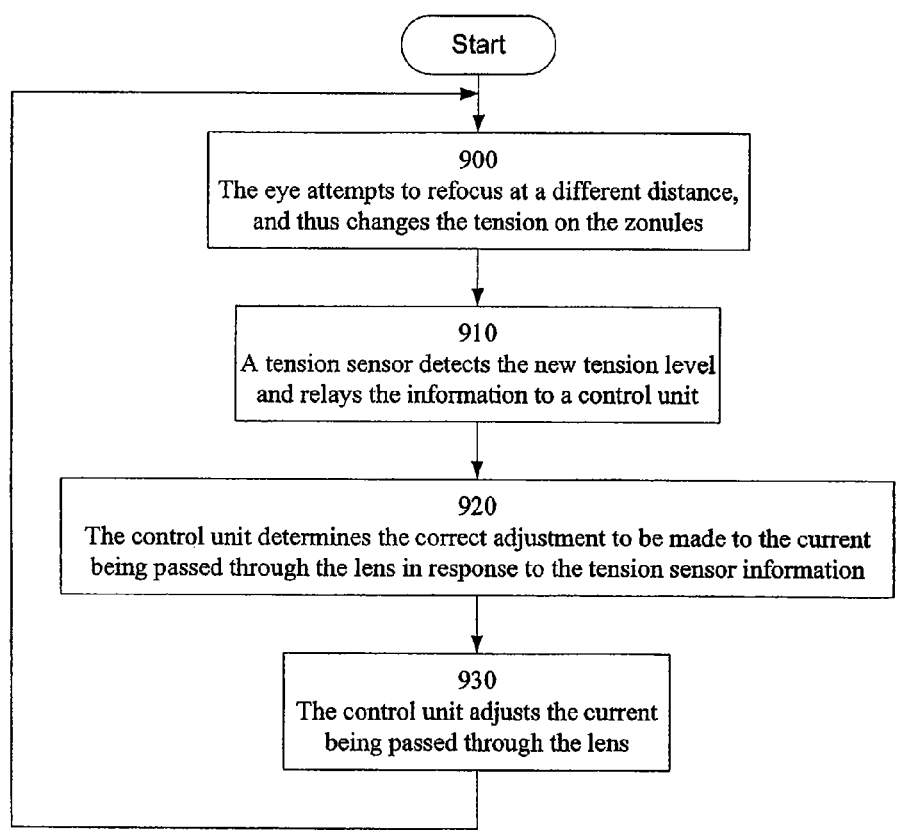
FIG. 9 is a flow chart of the process of accommodation in response to electrical signals in accordance with one embodiment of the present invention.

The process of accommodation in response to electrical signals in accordance with one embodiment is shown in FIG. 9. At step 900, the eye attempts to refocus at a different distance, and thus changes the tension on the zonules. At step 910, a tension sensor detects the new tension level and relays the information to a control unit. The control unit preferably includes a power source; however, the control unit can include any suitable devices. At step 920, the control unit determines the correct adjustment to be made to the current being passed through the lens in response to the tension sensor information. At step 930, the control unit adjusts the current being passed through the lens and the process repeats at step 900.

Figure 10:
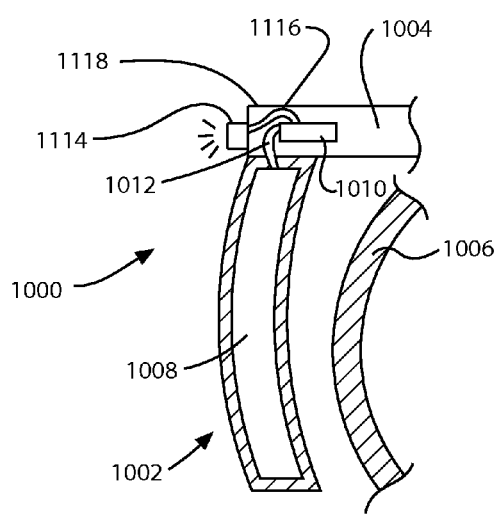
FIG. 10 is a side view in section of another embodiment of the present invention, showing the adjustable lens positioned relative to the eye.
Figure 11:
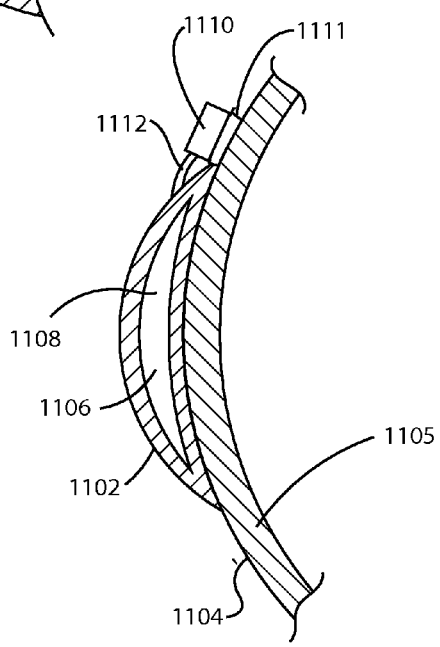
FIG. 11 is a side view in section of another embodiment of the present invention, showing the adjustable lens as a contact lens.

In another embodiment, as illustrated in FIGS. 10-11, the present invention can be used in an external lens. For example, the lens can be configured to be used with spectacles (FIG. 10) or as a contact lens (FIG. 11). The embodiments of FIG. 10-11 are configured to correct refractive errors in the eye. For example, the present embodiments can correct at least myopia, hyperopia and astigmatism. Furthermore, since these embodiments (as discussed in more detail below) can have their refractive properties altered, they are multi-focal lenses. Thus, these lenses can correct, among other disorders, presbyopia, or any combination of disorders.

When configured to be used in conjunction with spectacles 1000, lens 1002 is preferably coupled to a frame 1004 that positions the lens 1002 relative to the cornea 1006 of the eye in any suitable manner. As with previous embodiments, the lens 1002 has a chamber or area 1008 (or multiple chambers or areas, if desired) that is configured to hold a fluid or a mixture of fluids or any other suitable substance. Chamber 1008 preferably includes two immiscible (i.e., non-mixing) fluids of different refractive index (or other suitable optical property); however, the chamber 1008 is not required to include two immiscible fluids of different refractive index. Preferably, one of the immiscible fluids is an electrically conducting aqueous solution and the other an electrically non-conducting oil, contained in a short tube with transparent end caps, as described above; however, the immiscible fluids can be any suitable fluids and can be contained in any suitable container. The above description of the fluids is applicable to the present invention.

Preferably, as with the embodiments above, the shape of the lens 1002 can be adjusted by applying an electric field across the hydrophobic coating such that it becomes less hydrophobic (a process called "electrowetting" that results from an electrically induced change in surface-tension); however, the shape of the lens 1002 can be adjusted by applying an electric field across any suitable portion of the lens 1002. Preferably, as a result of this change in surface-tension, the aqueous solution begins to wet the sidewalls of the tube, altering the radius of curvature of the meniscus between the two fluids and hence the focal length of the lens. Increasing the applied electric field can preferably cause the surface of the initially convex lens to become less convex, substantially flat or concave; however increasing the applied electric field can cause the surface of the lens to change in any suitable manner. Preferably, decreasing the applied electric field has the opposite effect, enabling the lens 1002 to transition smoothly from being convergent to divergent, or vice versa, and back again repeatably. Thus, allowing the lens 1002 to repeatably focus on near and/or far objects.

The focal range of the lens 1002 can be any suitable range and can extend to infinity. Further, switching over the full focal range can occur in less than 10 ms or any other suitable amount of time. Preferably, lens 1002 is controlled by a DC voltage and presents a capacitive load; however, the lens 1002 can be controlled by any suitable voltage and operate with any suitable electrical properties.

Lens 1002 is electrically coupled to a power source 1010 by electrically conductive line 1012; however, lens 1002 can be coupled to power source 1010 in any suitable manner. Preferably, power source 1010 is rechargeable through direct electrical current, induction or other suitable means such as generating and storing electrical energy using eye and/or head movement to provide the energy to drive the generator; however, the power source 1010 can be non-rechargeable, if desired. Power source 1010 is preferably located on the frame 1004 of spectacles 1000; however, the power source 1010 can be positioned in any suitable location. The power source 1010 preferably includes a signal generator which can supply current to the lens 1002 via electrically conductive line 1012; however, the power source 1010 can be without a signal generator, if desired, or can supply control signals to the lens 1002 in any suitable manner.

Preferably, the power source 1010 is coupled to a sensor 1114 by electrically conductive line 1116; however, the power source 1010 can be coupled to sensor 1116 in any suitable manner (e.g. wirelessly). The sensor 1114 is preferably a distance sensor positioned on the front 1118 of frame 1004 so that the sensor 1114 detects the distance of an object away from the eye (such as a laser range finder); however, the sensor 1114 can be any suitable sensor type. Preferably, the sensor 1114 is positioned relative to the eye such that it detects the distance a specific object is from the eye and adjusts the lens 1002 accordingly; however, the sensor 1114 can detect a manual attempt to adjust the lens 1002 (e.g., input through a wireless controller or direct push buttons) or any other suitable input. The information detected at the sensor 1114 is relayed to the power source 1010 via line 1116, and the signal generator of the power source 1010 generates a signal in accordance with the information. The signal is sent and passed through the lens 1002, which preferably changes shape as a result of the electrical current flowing through it; however, the lens 1002 could change its index of refraction in response to the electrical current flowing through it or change its focal length in any other suitable manner. Preferably, line 1012 includes two separate electrical pathways that electrically couple to lens 1102 at different, preferably substantially opposite, locations so that one of the pathways can serve as a ground wire; however, the lens 1002 can be grounded in any other suitable manner to enable current supplied via line 1012 to flow through the lens 1002.

Additionally, the lens 1002 can be wirelessly coupled to a sensor, such as sensor 68, described above and adjust based on signals from the cilliary muscles and/or the zonules. Response of lens 1002 may vary from that of the natural lens; however, as with lenses described above, the neural systems which control the ciliary muscle 22 (and therefore the tension on the zonules 20), are provided with feedback from the optic nerve and visual neural pathways. As a result, the neural system can learn and adjust to the characteristics of the lens 1002.

FIG. 11 illustrates another embodiment of the present invention, where the lens 1102 is a contact lens that is positioned on the external surface 1104 of the cornea 1105.

As with lens 1002, lens 1102 includes a chamber or area 1106 (or multiple chambers or areas, if desired) having a fluid 1108 therein. Preferably, fluid 1108 is the same as the fluid described above for lens 1002 and operates in the substantially the same manner; however, any suitable fluid and/or substance or combination thereof can be used.

As described above, lens 1102 is coupled to a power source 1110 via an electrical wire 1112, or by any other suitable means. The power source 1110 is coupled to lens 1102 in any suitable manner (e.g., attached to a protrusion 1111). Power source 1110 and electrical wire 1112 are configured and operate in substantially the same manner as described above for lens 1002. Any description of lens 1002 and power source 1010 is applicable to lens 1102 and power source 1110.

Furthermore, lens 1102 can have a distance sensor (or any other sensor) that is located outside the eye and wirelessly coupled or directly wired to power source 1110, as described above. The sensor can be a sensor coupled to the lens 1102 (or any other suitable place on or adjacent the eye) or it can be located in the eye, and operate in substantially the same manner as sensors described above.

Additionally, both lens 1002 and 1102 can have their respective refractive properties altered in any manner described herein and are not limited the specific descriptions above. For example, lens 1102 and lens 1002 can have their respective refractive properties altered by changing the fluidic pressure as described above.

Figure 14:
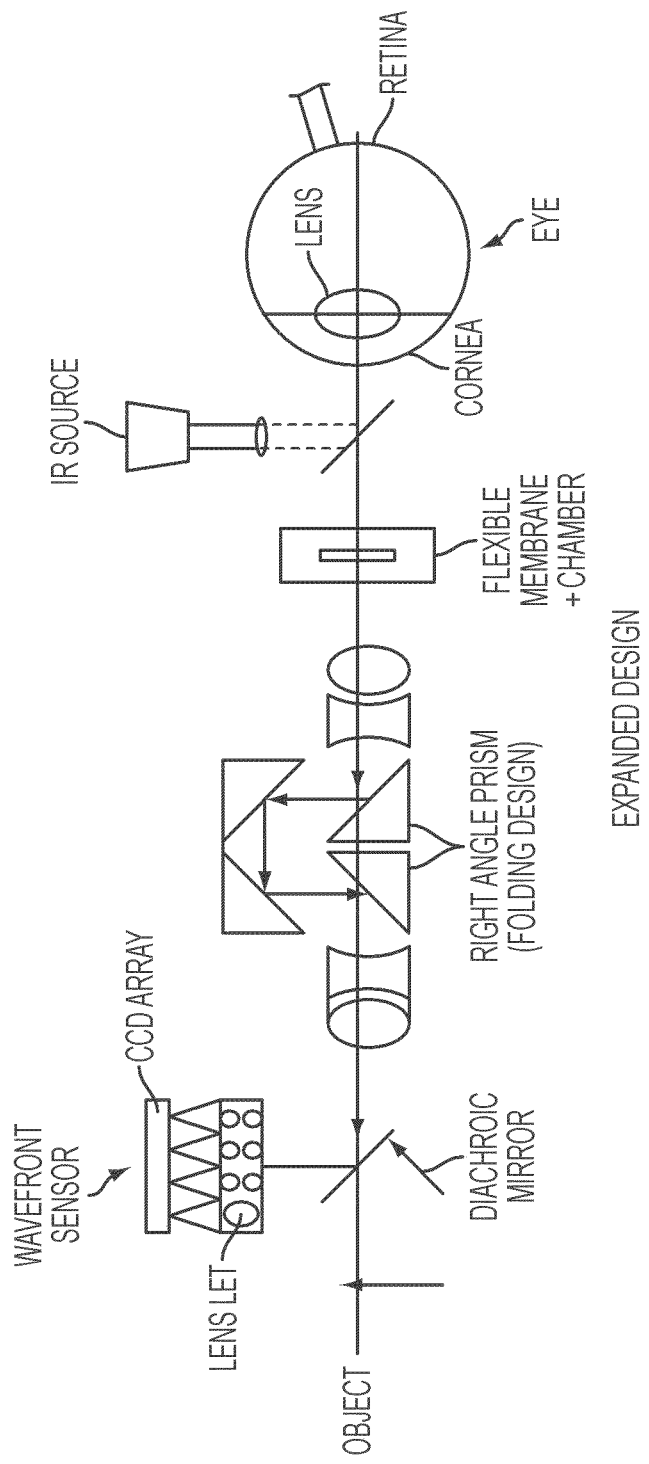
FIG. 14 illustrates another embodiment of the present invention in which a device is shown that is capable of automatically correcting all refractive errors of an eye.

As shown in FIGS. 12, 13, and 14, one embodiment of the automated system of the present invention comprises flexible membrane, similar to the embodiments described above, attached to a solid chamber where the membrane's surface can be made to act as a positive or negative surface by altering the fluid pressure inside the chamber.

The membrane can be constructed from any transparent elastomeric material. Depending on the membrane's peripheral attachment (e.g. circular) the membrane acts as a spherical (plus or minus 35.00 D) lens or (plus or minus 8.00 D) cylindrical lens when its attachment is rectangular (FIGS. 12-13).

By combining one spherical and two cylindrical lens-membranes, positioned 45 degrees to one another, one can correct all low order aberration of the refractive errors.

Using a non-uniform thickness membrane or an additional lens module one can also correct the higher order aberrations of refractive errors and creation of an achromatic lens. The flexible membrane lens is adjusted to null the wavefront error of the eye.

When this system is combined with a relay telescope, the image of the eye pupil can be projected onto a wavefront sensor via a diachroic mirror to analyze the shape of the wavefront (FIG. 14) while the person sees a near or distant object. The present system eliminates deformable mirrors and scanning parts; therefore it is a compact and stable unit.

The sensor in return corrects automatically all refractive errors of an eye by adding or subtracting fluid from the chamber holding the flexible membrane, thereby adjusting the curvature of the flexible membranes.

The final information is equal to the eye's refractive power of an eye for any given distance. Because of its simple design and light weight of the system both eyes of a person can be corrected simultaneously.

Additional application of this concept besides vision correction and photography includes microscope lenses, operating microscope, a lensometer capable of measuring accurately various focal points (power) of a multifocal lens or a multifocal diffractive lens, liquid crystal lenses etc. known in the art. A combination of the plus and minus flexible membrane lenses can also provide a lightweight telescope. Others include hybrid combination of this technology with diffractive, refractive and liquid crystal lenses.

Figure 15:
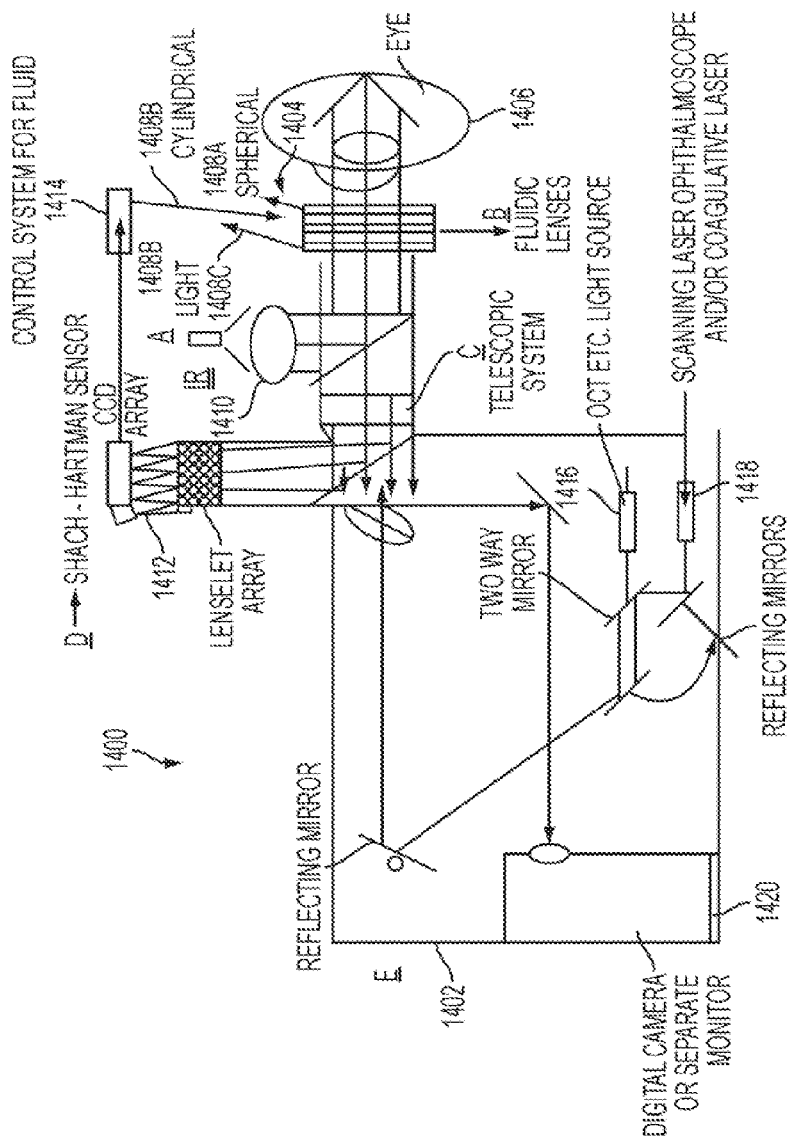
FIG. 15 illustrates another embodiment of the present invention in which a fluidic adaptive optic fundus camera is shown.

FIG. 15 illustrates another embodiment of the present invention. In particular, FIG. 15 illustrates a system 1400 in which a fundus camera 1402 uses a fluidic adaptive optic lens 1404. Adjacent the patient's eye 1406, are the three fluidic lenses 1408A-C. Preferably, one of the fluidic lenses is a spherical lens 1408A, and two of the lenses are cylindrical lenses 1408B and 1408C. However, the system can include any number of suitable lenses. In an exemplary embodiment, the spherical lens 1408A is disposed in a first plane, the first cylindrical lens 1408B is disposed in a second plane, and the second cylindrical lens 1408C is disposed in a third plane. Each of the first, second, and third planes are oriented parallel or generally parallel to one another. Also, the first cylindrical lens 1408B has a first axis and the second cylindrical lens 1408C has a second axis. The first axis of the first cylindrical lens 1408B is disposed at an angle of approximately 45 degrees relative to the second axis of the second cylindrical lens 1408C. In addition, in an exemplary embodiment, the first plane of the spherical lens 1408A is disposed closer to the eye 1406 than the second plane of the first cylindrical lens 1408B and the third plane of the second cylindrical lens 1408C. As such, in this exemplary embodiment, the cylindrical lenses 1408B, 1408C are positioned at 45 degrees or about 45 degrees relative to each other, and are disposed in front of the spherical lens 1408A (i.e., farther from the eye 1406).

The three lens system forms a telescopic system that transmits the light from IR light 1410 reflected from the eye and through the three lenses to a Shack-Hartmann sensor 1412. The Shack-Hartmann sensor is connected to control system 1414 through a charge-coupled device (CCD) array. The Shack-Hartmann sensor and the control system controls the amount of fluid injected and/or removed in the three fluidic lenses. Preferably, the control system includes (or is in communication with) a pump (not shown) which injects and withdraws fluid from a container (not shown). By injecting and withdrawing fluid from the lenses, high and low order aberrations are eliminated prior to the photography, since the fluidic lenses are capable of adjusting to the specific needs of the eye, in the same manner as described above.

Fundus camera 1402 is preferably equipped with white flush or a scanning laser ophthalmoscope or various lasers with different wavelengths from ultraviolet to infra-red wave length to obtain various visual information from the retina, choroid and optic nerve head. At low energy, the coagulative laser 1418 in FIG. 15 acts as an aiming beam, so it may be both coagulative and non-coagulative depending on its energy level. An Optical coherence tomography (OCT) 1416 or a laser can replace the scanning laser 1418 (or coagulative laser) to obtain two or three dimensional histological images from the eye structures or the laser can perform a precise coagulation of the retina along with the OCT images.

The fundus camera 1402 is also connected to a digital camera 1420 and/or a visualization monitor. Therefore, the images captured by the fundus camera can be viewed in real time or captured for viewing at a later time.

Additionally, the camera position can be moved into any desired position by a two way mirror that is positioned behind the fluidic lens.

The present system results in a compact, lightweight, precise and inexpensive advanced camera system eliminating the need for the complex prior technology which uses deformable mirrors.

Figure 16:
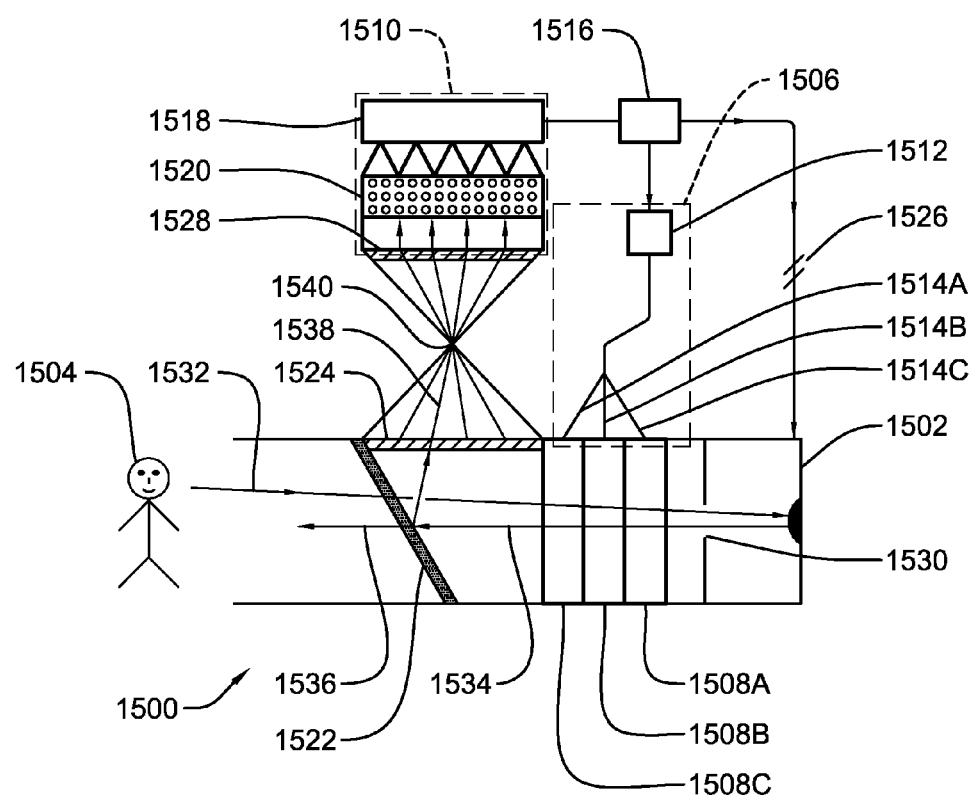
FIG. 16 illustrates yet another embodiment of the present invention in which an automated camera system is shown, wherein the automated camera system comprises a plurality of fluidic lenses.

FIG. 16 illustrates yet another embodiment of the present invention. In particular, FIG. 16 illustrates an automated camera system 1500, wherein the light waves entering a camera are corrected using a plurality of fluidic lenses 1508A, 1508B, and 1508C. As shown in FIG. 16, the automated camera system 1500 generally comprises a camera 1502 configured to capture an image of an object 1504; a plurality of fluidic lenses (e.g., three fluidic lenses 1508A, 1508B, and 1508C) disposed between the camera 1502 and the object 1504, each of the plurality of fluidic lenses 1508A, 1508B, and 1508C having a respective chamber that receives a fluid therein; a fluid control system 1506 operatively coupled to each of the plurality of fluidic lenses 1508A, 1508B, and 1508C, the fluid control system 1506 configured to insert an amount of the fluid into the respective chamber of each of the plurality of fluidic lenses 1508A, 1508B, and 1508C, or remove an amount of the fluid from the respective chamber of each of the plurality of fluidic lenses 1508A, 1508B, and 1508C, in order to change the shape of each of the plurality of fluidic lenses 1508A, 1508B, and 1508C in accordance with the amount of fluid therein; and a Shack-Hartmann sensor assembly 1510 operatively coupled to the fluid control system 1506, the Shack-Hartmann sensor assembly 1510 by means of the fluid control system 1506 configured to automatically control the amount of the fluid in the respective chamber of each of the plurality of fluidic lenses 1508A, 1508B, and 1508C, thereby automatically focusing the camera 1502 so that the image captured of the object 1504 is in focus. The camera 1502 may comprise any one of: (i) a digital camera for photography, (ii) a camera for automated microscopy, (iii) an optical coherence tomography (OCT) camera, (iv) a video surveillance camera, or (v) a camera for any other form of imaging, such as telesystem imager or a laser scanner, etc. The camera 1502 may record visible light images, infrared (IR) light images, ultraviolet (UV) light images, etc. Advantageously, the camera 1502 has no moving parts and is automatically focused by means of the plurality of fluidic lenses 1508A, 1508B, and 1508C.

As shown in FIG. 16, the camera 1502 comprises a camera aperture 1530 that allows light rays to pass therethrough. The camera 1502 may also comprise a standard lens that is disposed behind the plurality of fluidic lenses 1508A, 1508B, and 1508C.

In the automated camera system 1500 of FIG. 16, the three fluidic lenses may include a spherical lens 1508A, a first cylindrical lens 1508B, and a second cylindrical lens 1508C. In the illustrated embodiment, the spherical lens 1508A, which is closest to the camera 1502, may be a spherical lens as illustrated in FIG. 12. Similarly, in the illustrated embodiment, the first and second cylindrical lenses 1508B, 1508C, which are disposed in front the spherical lens 1508A, may each be a cylindrical lens as illustrated in FIG. 13. In an exemplary embodiment, the spherical lens 1508A is disposed in a first plane, the first cylindrical lens 1508B is disposed in a second plane, and the second cylindrical lens 1508C is disposed in a third plane. Each of the first, second, and third planes are oriented parallel or generally parallel to one another. Also, the first cylindrical lens 1508B has a first axis and the second cylindrical lens 1508C has a second axis. The first axis of the first cylindrical lens 1508B is disposed at an angle of approximately 45 degrees relative to the second axis of the second cylindrical lens 1508C. In addition, in an exemplary embodiment, the first plane of the spherical lens 1508A is disposed closer to the camera 1502 than the second plane of the first cylindrical lens 1508B and the third plane of the second cylindrical lens 1508C.

Referring again to the illustrative embodiment of FIG. 16, it can be seen that the fluid control system 1506 comprises a pump 1512 and a plurality of fluid distribution lines 1514A, 1514B, 1514C. Each of the plurality of fluid distribution lines 1514A, 1514B, 1514C fluidly connects the pump to a respective one of the plurality of fluidic lenses 1508A, 1508B, and 1508C. The pump 1512 adjusts the refractive power of the plurality of fluidic lenses 1508A, 1508B, and 1508C by inserting an amount of fluid into, or removing an amount of fluid from, each of the respective chambers of the plurality of fluidic lenses 1508A, 1508B, and 1508C.

With reference again to FIG. 16, it can be seen that the illustrative automated camera system 1500 further includes a data processing device 1516, which may be in the form of a personal computing device or personal computer. The data processing device 1516 (i.e., computer) of the automated camera system 1500 may comprise a microprocessor for processing data, memory (e.g., random access memory or RAM) for storing data during the processing thereof, and data storage device(s), such as one or more hard drives, compact disk drives, floppy disk drives, flash drives, or any combination thereof. At least one visual display device (i.e., monitor or display) may be operatively coupled to the data processing device 1516 (i.e., computer). Also, a plurality of user data input devices, such as a keyboard and a mouse, may be operatively coupled to the data processing device 1516 (i.e., computer) so that a user is able to enter data into the data processing device 1516.

As shown in FIG. 16, the data processing device 1516 (i.e., computer) is operatively connected to the pump 1512 of the fluid control system 1506 by, for example, a wired connection or a wireless connection. Also, the data processing device 1516 (i.e., computer) is operatively connected to the Shack-Hartmann sensor assembly 1510 by a wired connection or a wireless connection. The data processing device (i.e., computer) is specifically programmed to control the operation of the pump 1512 of the fluid control system 1506 based upon one or more output signals from the Shack-Hartmann sensor assembly 1510. Also, as shown in FIG. 16, the data processing device 1516 (i.e., computer) is operatively coupled to the camera 1502 by, for example, a wired connection or a wireless connection. When the Shack-Hartmann sensor assembly 1510 indicates to the data processing device 1516 (i.e., computer) that the object 1504 is in focus for the camera 1502, the data processing device 1516 is specially programmed to emit one or more initiation signals to the camera 1502 instructing the camera to capture the image of the object 1504. That is, the data processing device 1516 initiates a recording by the camera 1502 (e.g., a single photograph or a movie/video) or initiates an action, such as surveillance of an area with in-focus photos (i.e., if the camera 1502 is in the form of a video surveillance camera). As also shown in FIG. 16, an on-off switch 1526 may be provided to activate or deactivate the functionality of the automated camera system 1500 described herein. That is, when the on-off switch 1526 is in the "on" position, the data processing device 1516 automatically controls the operation of the camera 1502 by means of the one or more initiation signals that automatically initiate the capturing of the image (i.e., the automatic mode). Conversely, when the on-off switch 1526 is in the "off" position, the camera 1502 is in the non-automatic mode, whereby the operation of the camera 1502 is manually controlled by a user thereof (e.g., the user is required to manually focus the camera 1502 in the non-automatic mode).

In FIG. 16, it can be seen that the Shack-Hartmann sensor assembly 1510 comprises a charge-coupled device (CCD) array 1518 and a lenslet array 1520. The charge-coupled device (CCD) array 1518 of the Shack-Hartmann sensor assembly 1510 is operatively connected to the data processing device 1516 (i.e., computer) by, for example, a wired connection or a wireless connection. Also, as shown in FIG. 16, the automated camera system 1500 further includes a dichroic mirror 1522 disposed in front of the plurality of fluidic lenses 1508A, 1508B, and 1508C. The dichroic mirror 1522 is located between the plurality of fluidic lenses 1508A, 1508B, and 1508C and the lenslet array 1520 of Shack-Hartmann sensor assembly 1510 in the path of the light. The dichroic mirror 1522 allows the light rays 1532 from the external light source outside the automated camera system 1500 to pass therethrough (as indicated by arrow 1532 in FIG. 16). The external light source could be sunlight, an artificial flash light, or an external source that generates an infrared light. The external light source illuminates the object 1504 that is being photographed or recorded by the camera 1502. The automated camera system 1500 additionally includes a first diffractive lens 1524 or a holographic optical element (HOE) disposed between the dichroic mirror 1522 and the lenslet array 1520 in the path of the light. A holographic optical element (HOE) is essentially a diffractic element, but it is made with the technique of a hologram, which results in a very thin diffractive film. A holographic optical element (HOE) is easily reproducible and inexpensive to fabricate. The first diffractive lens 1524 or holographic optical element (HOE) directs the portion 1538 of the light that is reflected from the dichroic mirror 1522 to a single focal point 1540. After passing through the single focal point 1540, the reflected light passes through a second diffractive lens 1528 before entering the lenslet array 1520 of the Shack-Hartmann sensor assembly 1510. The first and second diffractive lens 1524, 1528 are required in the automated camera system 1500 in order to maintain the fidelity of the reflected light 1538. In order to avoid obscuring the image being captured by the camera 1502, the Shack-Hartmann sensor assembly 1510 must be located outside of the direct focal line of the camera 1502.

Now, with reference again to FIG. 16, the functionality of the automated camera system 1500 of FIG. 16 will be described. Initially, as explained above, the light rays 1532 from the external light source pass through dichroic mirror 1522 and the plurality of fluidic lenses 1508A, 1508B, and 1508C, and then, are reflected back from the camera 1502 (i.e., reflected light 1534 in FIG. 16). As shown in FIG. 16, the light waves or rays 1534 that are reflected back from the camera 1502 initially pass through the plurality of fluidic lenses 1508A, 1508B, and 1508C. In particular, the light waves pass through the spherical fluidic lens 1508A first, then followed by the first cylindrical fluidic lens 1508B, and finally the second cylindrical fluidic lens 1508C. After passing through the plurality of fluidic lenses 1508A, 1508B, and 1508C, a first portion 1536 of the reflected light 1534 passes back through the dichroic mirror 1522 to the outside, while a second portion 1538 of the reflected light 1534 is reflected by the dichroic mirror 1522 through the first diffractive lens 1524. As explained above, the first diffractive lens 1524 directs the second portion 1538 of the light that is reflected from the dichroic mirror 1522 to a single focal point 1540. After passing through the single focal point 1540, the reflected light 1538 passes through a second diffractive lens 1528 before entering the lenslet array 1520 of the Shack-Hartmann sensor assembly 1510. After the light waves are transmitted to the lenslet array 1520 of the Shack-Hartmann sensor assembly 1510, a light spotfield is created on the charge-coupled device (CCD) array or CCD camera 1518 of the Shack-Hartmann sensor assembly 1510 so that the intensity and location of each light spot in the spotfield may be determined. When light spots in the spotfield are crisp and clear in the Shack-Hartmann sensor assembly 1510, they are in focus. Conversely, when light spots in the spotfield are fuzzy in the Shack-Hartmann sensor assembly 1510, they are not in focus. When all of the light spots in the spotfield are in focus, the subject of the photography (i.e., object 1504) is in focus for the camera 1502. Upon determining the intensity and location information from the spotfield, the Shack-Hartmann sensor assembly 1510, by means of the data processing device 1516, controls the refractive power of the lenses 1508A, 1508B, and 1508C through the computerized fluid pump 1512 connected to the fluidic lenses 1508A, 1508B, and 1508C. When the Shack-Hartmann sensor assembly 1510 indicates that the object 1504 of view (a landscape, person, etc.) is in focus for the camera 1502, the data processing device 1516 is specially programmed to emit one or more initiation signals to the camera 1502 so as to initiate the recording of a photo or video, with a flash or without a flash light using infra-red light.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. An automated camera system, comprising:
   a camera configured to capture an image of an object;
   at least one fluidic lens disposed between the camera and the object, the at least one fluidic lens having a chamber that receives a fluid therein;
   a fluid control system operatively coupled to the at least one fluidic lens, the fluid control system configured to insert an amount of the fluid into the chamber of the at least one fluidic lens, or remove an amount of the fluid from the chamber of the at least one fluidic lens, in order to change the shape of the at least one fluidic lens in accordance with the amount of fluid therein, the fluid control system comprising a pump and one or more fluid distribution lines, at least one of the one or more fluid distribution lines fluidly coupling the pump to the at least one fluidic lens so that the pump is capable of adjusting refractive power of the at least one fluidic lens;
   a Shack-Hartmann sensor assembly operatively coupled to the fluid control system, the Shack-Hartmann sensor assembly comprising a charge-coupled device (CCD) array and a lenslet array, the Shack-Hartmann sensor assembly by means of the fluid control system configured to automatically control the amount of the fluid in the chamber of the at least one fluidic lens, thereby automatically focusing the camera so that the image captured of the object is in focus, and wherein light is reflected back from the camera, and the lenslet array is disposed in a path of the reflected light entering the Shack-Hartmann sensor assembly; and
   a data processing device operatively coupled to the pump of the fluid control system, the charge-coupled device (CCD) array of the Shack-Hartmann sensor assembly, and the camera, the data processing device being configured to control an operation of the pump of the fluid control system based upon one or more output signals from the Shack-Hartmann sensor assembly, and wherein, when the Shack-Hartmann sensor assembly indicates to the data processing device that the object is in focus for the camera, the data processing device is configured to emit an initiation signal to the camera instructing the camera to capture the image of the object.

2. The automated camera system of claim 1, further comprising a dichroic mirror disposed in the path of the reflected light between the at least one fluidic lens and the lenslet array.

3. The automated camera system of claim 2, further comprising a first diffractive lens or a first holographic optical element disposed in the path of the reflected light between the dichroic mirror and the lenslet array.

4. The automated camera system of claim 3, further comprising a second diffractive lens or a second holographic optical element disposed in the path of the reflected light between the first diffractive lens or the first holographic optical element and the lenslet array.

5. An automated camera system, comprising:
a camera configured to capture an image of an object, the camera comprising one of: (i) a digital camera for photography, (ii) a camera for automated microscopy, (iii) an optical coherence tomography (OCT) camera, and (iv) a video surveillance camera;
a plurality of fluidic lenses disposed between the camera and the object, each of the plurality of fluidic lenses having a respective chamber that receives a fluid therein;
a fluid control system operatively coupled to each of the plurality of fluidic lenses, the fluid control system configured to insert an amount of the fluid into the respective chamber of each of the plurality of fluidic lenses, or remove an amount of the fluid from the respective chamber of each of the plurality of fluidic lenses, in order to change the shape of each of the plurality of fluidic lenses in accordance with the amount of fluid therein;
a Shack-Hartmann sensor assembly operatively coupled to the fluid control system, the Shack-Hartmann sensor assembly by means of the fluid control system configured to automatically control the amount of the fluid in the respective chamber of each of the plurality of fluidic lenses, thereby automatically focusing the camera so that the image captured of the object is in focus; and
a data processing device operatively coupled to the fluid control system, the Shack-Hartmann sensor assembly, and the camera, wherein, when the Shack-Hartmann sensor assembly indicates to the data processing device that the object is in focus for the camera, the data processing device is configured to emit an initiation signal to the camera instructing the camera to capture the image of the object.

6. The automated camera system of claim 5, wherein the fluid control system comprises a pump and a plurality of fluid distribution lines, at least two of the plurality of fluid distribution lines fluidly coupling the pump to respective ones of the plurality of fluidic lens so that the pump is capable of adjusting refractive power of the plurality of fluidic lens.

7. The automated camera system of claim 6, wherein the data processing device is further operatively coupled to the pump of the fluid control system, the data processing device being configured to control an operation of the pump of the fluid control system based upon one or more output signals from the Shack-Hartmann sensor assembly.

8. The automated camera system of claim 7, wherein the Shack-Hartmann sensor assembly comprises a charge-coupled device (CCD) array and a lenslet array, and wherein the charge-coupled device (CCD) array of the Shack-Hartmann sensor assembly is operatively coupled to the data processing device.

9. The automated camera system of claim 8, wherein light is reflected back from the camera, and wherein the lenslet array is disposed in a path of the reflected light entering the Shack-Hartmann sensor assembly; and wherein the automated camera system further comprises a dichroic mirror disposed in the path of the reflected light between the plurality of fluidic lenses and the lenslet array.

10. An automated camera system, comprising:
a camera configured to capture an image of an object;
three fluidic lenses disposed between the camera and the object, each of the three fluidic lenses having a respective chamber that receives a fluid therein, the three fluidic lenses including a spherical lens disposed in a circular container, a first cylindrical lens disposed in a first rectangular container, and a second cylindrical lens disposed in a second rectangular container;
a fluid control system operatively coupled to each of the three fluidic lenses, the fluid control system configured to insert an amount of the fluid into the respective chamber of each of the three fluidic lenses, or remove an amount of the fluid from the respective chamber of each of the three fluidic lenses, in order to change the shape of each of the three fluidic lenses in accordance with the amount of fluid therein;
a Shack-Hartmann sensor assembly operatively coupled to the fluid control system, the Shack-Hartmann sensor assembly by means of the fluid control system configured to automatically control the amount of the fluid in the respective chamber of each of the three fluidic lenses, thereby automatically focusing the camera so that the image captured of the object is in focus; and
a data processing device operatively coupled to the fluid control system, the Shack-Hartmann sensor assembly, and the camera, wherein, when the Shack-Hartmann sensor assembly indicates to the data processing device that the object is in focus for the camera, the data processing device is configured to emit an initiation signal to the camera instructing the camera to capture the image of the object.

11. The automated camera system of claim 10, wherein the spherical lens is disposed in a first plane, the first cylindrical lens is disposed in a second plane, and the second cylindrical lens is disposed in a third plane, and wherein each of the first, second, and third planes are oriented generally parallel to one another.

12. The automated camera system of claim 11, wherein the first cylindrical lens has a first axis and the second cylindrical lens has a second axis, the first axis of the first cylindrical lens being disposed at an angle of approximately 45 degrees relative to the second axis of the second cylindrical lens.

13. The automated camera system of claim 11, wherein the first plane of the spherical lens is disposed closer to the camera than the second plane of the first cylindrical lens and the third plane of the second cylindrical lens.

14. The automated camera system of claim 10, wherein the camera comprises one of: (i) a digital camera for photography, (ii) a camera for automated microscopy, (iii) an optical coherence tomography (OCT) camera, and (iv) a video surveillance camera.

* * * * *